United States Patent [19]

Tankovich et al.

[11] Patent Number: 5,752,948
[45] Date of Patent: May 19, 1998

[54] HAIR REMOVAL METHOD

[75] Inventors: Nikolai Tankovich; Richard G. Episcopo, both of San Diego; Lawrence Sverdrup, Poway, all of Calif.

[73] Assignee: ThermoLase Corporation, San Diego, Calif.

[21] Appl. No.: 492,283

[22] Filed: Jun. 19, 1995

Related U.S. Application Data

[63] Continuation-in-part of Ser. No. 280,928, Jul. 26, 1994, abandoned, and Ser. No. 5,810, Jan. 19, 1993, Pat. No. 5,425,728, which is a continuation-in-part of Ser. No. 783,789, Oct. 29, 1991, Pat. No. 5,226,907.

[51] Int. Cl.$^6$ .............................. A61B 17/36; A61B 17/50
[52] U.S. Cl. .................................... 606/9; 606/133
[58] Field of Search ........................ 606/9–19, 131, 606/133; 128/898; 607/88–90

[56] References Cited

U.S. PATENT DOCUMENTS

| | | |
|---|---|---|
| 3,538,919 | 11/1970 | Mayer . |
| 3,693,623 | 9/1972 | Harte et al. . |
| 3,769,963 | 11/1973 | Goldman et al. ............ 606/9 |
| 3,794,028 | 2/1974 | Mueller et al. . |
| 3,834,391 | 9/1974 | Block . |
| 3,900,034 | 8/1975 | Katz et al. . |
| 4,336,809 | 6/1982 | Clark . |
| 4,388,924 | 6/1983 | Weissman et al. . |
| 4,461,294 | 7/1984 | Baron . |
| 4,608,978 | 9/1986 | Rohr . |
| 4,617,926 | 10/1986 | Sutton . |
| 4,712,543 | 12/1987 | Baron . |
| 4,813,412 | 3/1989 | Yamazaki . |
| 5,059,192 | 10/1991 | Zaias . |
| 5,226,907 | 7/1993 | Tankovich ................... 606/9 |
| 5,423,803 | 6/1995 | Tankovich et al. .......... 606/9 |
| 5,425,728 | 6/1995 | Tankovich ................... 606/9 |

FOREIGN PATENT DOCUMENTS

| | | |
|---|---|---|
| 1041610 | 6/1974 | Canada . |
| 1208702 | 7/1986 | Canada . |
| D64967A2 | 4/1995 | European Pat. Off. . |
| 2267122 | 4/1975 | France . |
| 2595239 | 6/1982 | France . |
| 2590791 | 6/1987 | France . |
| 2515697 | of 0000 | Germany . |
| 3220962 | 6/1982 | Germany . |
| 0166123 | 12/1981 | Japan ............................ 606/9 |
| 63-249577 | 10/1988 | Japan . |
| 8002640 | 12/1980 | WIPO . |

(List continued on next page.)

OTHER PUBLICATIONS

Porphyrins in Tumer Phototherapy—Andereoni 1984—pp. 143–155.

Investigation and Therapy in Dermatology A. Anders, et al—Conf. Laser 77 Optics–Electronics (20–24 Jun. 1977).

*Primary Examiner*—Glenn K. Dawson
*Attorney, Agent, or Firm*—Fish & Richardson P.C.

[57] ABSTRACT

The present invention provides a process for the destruction of unwanted human hair. Hair ducts in a section of skin in which the unwanted hair are growing is contaminated with a contaminant having a high absorption at at least one frequency band of light. The skin section is then illuminated with light at the frequency band of high absorption so as to impact sufficient energy to the contaminant so as to cause death to the hairs growing in the ducts. In a preferred embodiment the contaminant is a mixture of 1 micron graphite particles in mineral oil and each section is illuminated with about 5 laser pulses at 1.06 micron wavelength produced by a Nd:YAG laser, each pulse having an energy density of about 3 Joules/cm$^2$ and a pulse width of about 10 nanoseconds. In another preferred embodiment the hairs in the section of skin being treated are pulled out prior to application of the contaminant so as to provide more space for the contaminant in the hair duct. In still another preferred embodiment a portion of the hairs below the skin surface is removed with a depilatory. In still another preferred embodiment $C_{60}$ molecules, buckey balls, are the absorbing elements in the contaminant.

44 Claims, 9 Drawing Sheets

FOREIGN PATENT DOCUMENTS

| | | |
|---|---|---|
| 8602783 | 5/1986 | WIPO . |
| WO90/11797 | 10/1990 | WIPO . |
| 9104073 | 4/1991 | WIPO . |
| WO91/13652 | 9/1991 | WIPO . |
| WO91/13653 | 9/1991 | WIPO . |
| WO93/21842 | 11/1993 | WIPO . |
| WO93/21992 | 11/1993 | WIPO . |

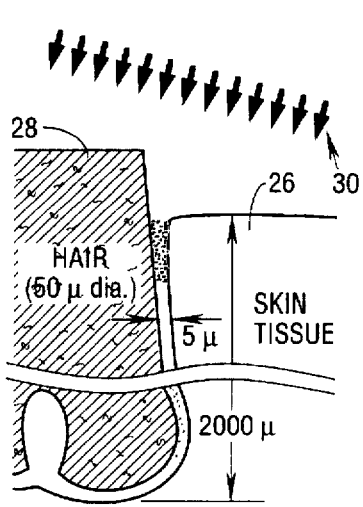
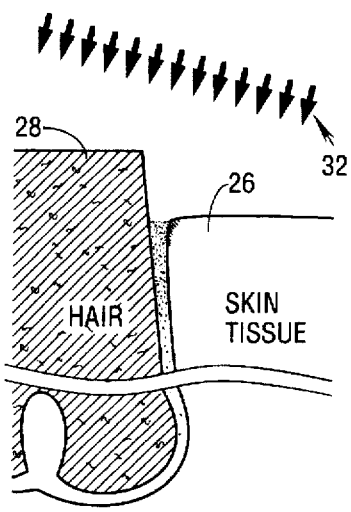
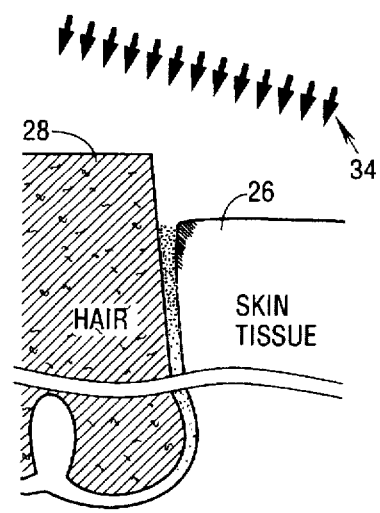
FIG. 6A  FIG. 6B  FIG. 6C
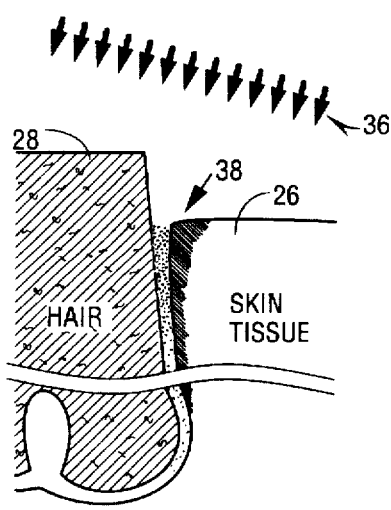
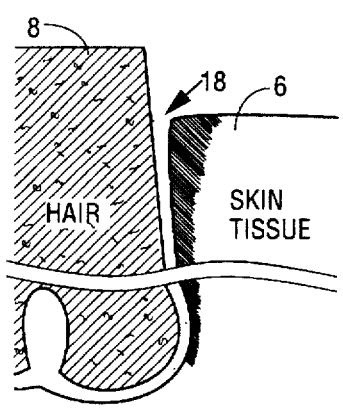
FIG. 6D  FIG. 6E

HAIR REMOVAL METHOD

This application is a continuation in part of my earlier filed applications Ser. No. 08/280,928 filed Jul. 26, 1994, now abandoned, and Ser. No. 08/005,810 filed Jan. 19, 1993, U.S. Pat. No. 5,425,728, which was a CIP of Ser. No. 07/783,789 filed Oct. 29, 1991 now U.S. Pat. No. 5,226,907 issued Jul. 13, 1993. This invention relates to devices and methods for hair removal and in particular to the use of laser devices for hair removal.

BACKGROUND OF THE INVENTION

The principal methods presently used for hair removal involve the use of electrolysis techniques. These techniques involve some pain, are time consuming, and demand a fair degree of expertise in their application and normally do not guarantee a permanent effect.

Laser use in medicine is well known. For example, lasers are used in surgery for both cutting and cauterization. Lasers have been used for many years for removing tattoos under the surface of the skin. In this case a laser beam penetrates the skin and is absorbed by and destroys the ink particle. A similar procedure has been used for years to remove birth marks where the laser is matched to an absorption peak of the erythrocyte's hemoglobin in the tiny capillaries under the skin to destroy the capillaries.

The prior art of hair removal also includes attempts at removing hair with laser beams. Three such techniques are described in the following U.S. Pat. Nos.: Weissman et. al., Method for Laser Depilation Device and Method, U.S. Pat. No. 4,388,924; Sutton, Depilation Device and Method, U.S. Pat. No. 4,617,926; and Mayer, Depilation by Means of Laser Energy, U.S. Pat. No. 3,538,919. All of these devices and methods teach the removal of hairs one hair at a time with a narrowly focused laser beam. Therefore, they are relatively inefficient and time consuming. A recent patent by Zaias, U.S. Pat. No. 5,059,192 issued Oct. 22,1991 discloses a process for using a laser beam matched to the melanin found at the base of the hair follicle and papilla.

It has been known for at least 20 years in the medical profession that selective absorption of laser radiation can sometimes be enhanced by the technique of staining pathological tissues with various vital dyes. (See Goldman U.S. Pat. No. 3,769,963).

In the graphite form of elementary carbon, each carbon atom has three near neighbors and a fourth neighbor at a considerably greater distance away, the two lengths being 1.42 A and 3.42 A, respectively. (10,000 angstrom equal 1 micron.) The network of the three nearest neighbors is planar and extends in the two directions of the plane to the boundaries of the solid. The binding forces between the planes are weak and the planes can slip past each other very readily. For this reason, graphite can be used as a lubricating material. Thin layers of graphite can be removed by abrasion and this property is exploited in the ordinary lead pencil in which motion of the graphite rod over paper causes thin layers of the solid to be rubbed off and spread on the paper. For many years laser workers have used paper thinly coated with small particles of graphite to examine the cross section power of certain laser beams. The energy of many laser beams is readily absorbed by the carbon particles and many of the particles react violently exploding off the paper and leaving "footprints" on the paper representative of the cross sectional power distribution of the laser beam.

What is needed is an improved hair removal process.

SUMMARY OF THE INVENTION

The present invention provides a process for the destruction of unwanted human hair. Hair ducts in a section of skin in which the unwanted hair are growing is contaminated with a contaminant having a high absorption at at least one frequency band of light. The skin section is then illuminated with light at the frequency band of high absorption so as to impart sufficient energy to the contaminant so as to cause death to the hairs growing in the ducts. In a preferred embodiment the contaminant is a mixture of 1 micron graphite particles in mineral oil and each section is illuminated with about 5 laser pulses at 1.06 micron wavelength produced by a Nd:YAG laser, each pulse having an energy density of about 3 Joules/cm$^2$ and a pulse width of about 10 nanoseconds. In another preferred embodiment the hairs in the section of skin being treated are pulled out prior to application of the contaminant so as to provide more space for the contaminant in the hair duct. In still another preferred embodiment a portion of the hairs below the skin surface is removed with a depilatory. In still another preferred embodiment $C_{60}$ molecules, buckey balls, are the absorbing elements in the contaminant.

BRIEF DESCRIPTION OF THE DRAWINGS

FIGS. 6A through 6E shows the graphite particles at various stages of fragmentation during a preferred process of hair removal.

FIRST PREFERRED EMBODIMENT

Our first preferred embodiment of the present invention, which was the subject of extensive animal tests, is described below:

Skin Preparation

Figure 1:
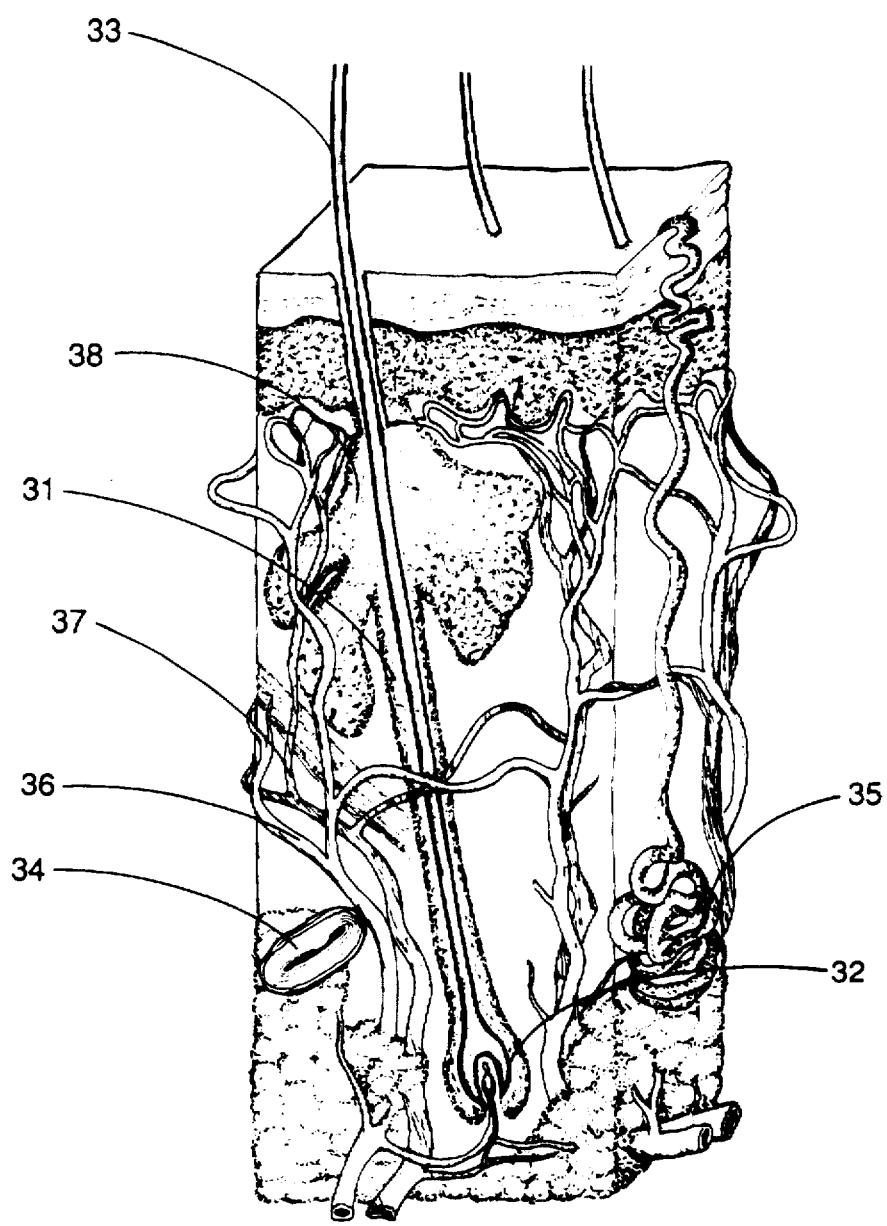
FIG. 1 is a drawing of a section of human skin showing a growing hair.

A section of human skin showing a cross section of one hair is shown in FIG. 1. A first preferred embodiment of the present invention can be described by reference to FIGS. 2–4. The figure shows the hair shaft 3, a nerve ending 4, a sweat gland 5 and arteries 6 and veins 7. First, a laser absorbing carbon suspension is prepared of carbon powder in mineral oil. The particle size of the powder preferably is about 10–20 nm and its concentration preferably is about 15% to 20% by volume.

Figure 2A:
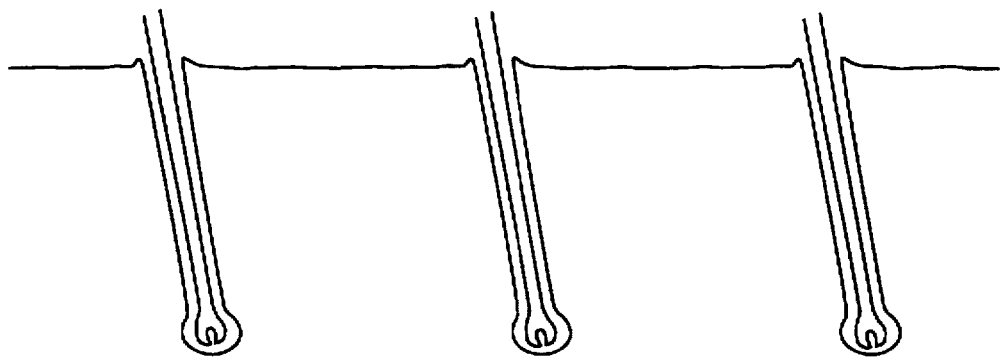
FIGS. 2A, B and C show a cross section of skin and 3 hairs during 3 stages of a process of one embodiment of the present invention.
Figure 2B:
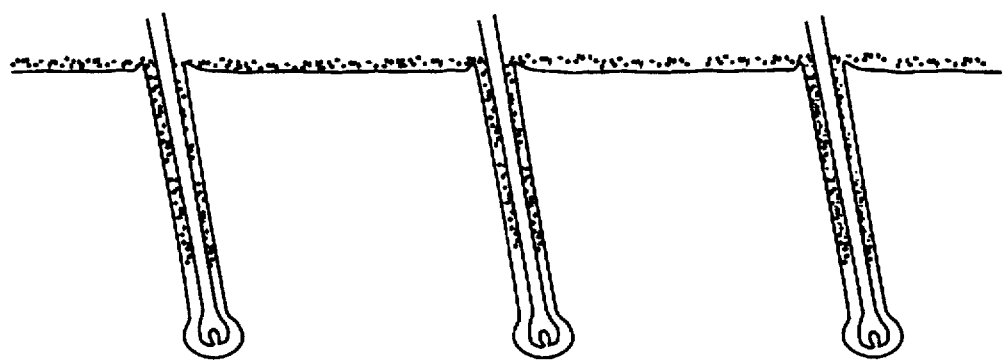
Figure 2C:
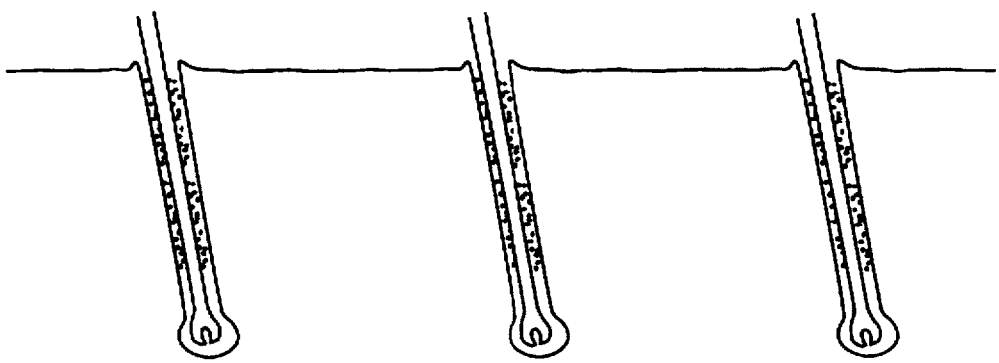

A clean section of skin is depicted in FIG. 2A. This suspension is rubbed on the skin with a massaging action so that portions of the carbon suspension infiltrates the hair ducts of the hair that is to be removed as shown in FIG. 2B. Next, the surface of the skin is cleaned preferably with an alcohol pad to make the skin surface clean but to leave the hair pores contaminated with the carbon suspension as shown in FIG. 2C.

Laser Application

The laser device used in this preferred embodiment is a $CO_2$ pulse laser which have the spikes in the range of 10.6 microns light of this wavelength will pass through the surface of the skin of a fair skin person and is readily absorbed in carbon. Laser parameters such as pulse width repetition rate can be selected to best fit the skin and hair types of the patients. The parameter for two specific examples which I have utilized with good results for hair removal are shown in Table 1:

TABLE 1

Parameters Preferred.

| | First Example | Second Example |
|---|---|---|
| Pulse Width | 275 ns | 200 µs |
| Repetition Rate | 30 Hz | 8 Hz |
| Laser Spot Size | 1 cm$^2$ | 1 cm$^2$ |
| Energy per Pulse | 0.1 Joule | 0.2 Joule |
| Scanning Rate | 20 seconds per 10 cm$^2$ | 30 seconds per 10 cm$^2$ |

Each point on the skin receives illumination for about 2 seconds and about 60 pulses and each square centimeter receives about 6 Joules. Some of the light is reflected some is absorbed directly in skin tissue and a significant percent of the energy of each pulse is absorbed in the carbon.

Figure 3:
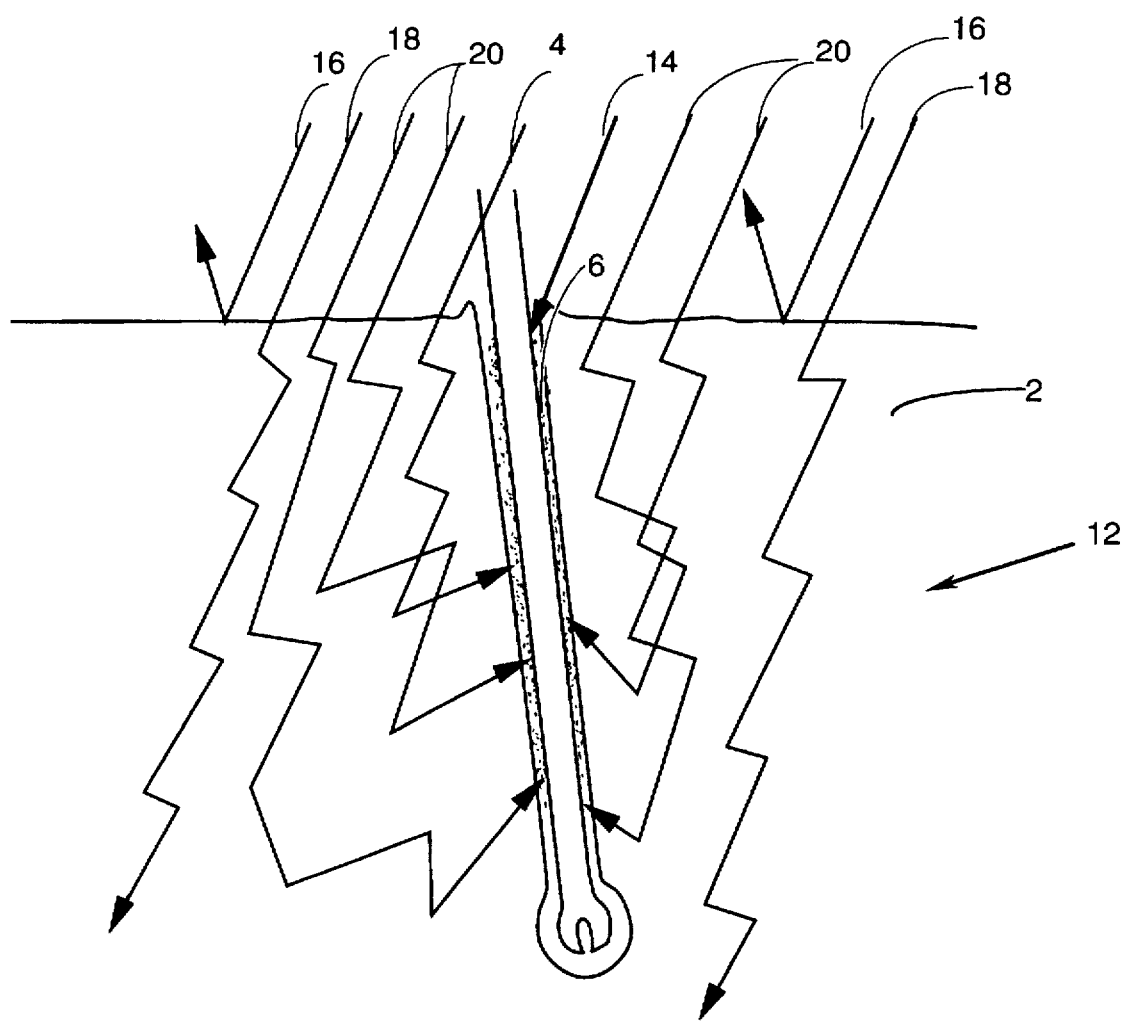
FIG. 3 shows qualitatively the paths of the photons of a laser pulse showing absorption in a carbon-oil suspension.

FIG. 3 shows a simplified view of a section of human skin and qualitatively the paths 12 of some of the photons of a laser pulse illuminating a section of skin 2 containing a hair duct with a hair 4 contaminated with carbon suspension 6. A few of the photons travel directly through the skin and are absorbed in the carbon (depicted by photon 14). Some are reflected from the skin surface (depicted by photons 16). Some are absorbed in the skin (depicted as photons 18) but a significant portion of the photons undergo diffuse reflectance in the skin and are absorbed in the carbon after several reflections.

Operating within the parameters specified is very important. They have been chosen to preferentially heat the suspension which in turns heats the hair follicles and the blood vessels feeding the follicle to temperatures high enough to kill the hair follicle and for the tissue feeding the follicles but to minimize the heating to the rest of the skin tissue. The pulse width is a most important parameter. It must be chosen so that a large amount of energy is deposited in the suspension quickly so that the temperature of the suspension rises rapidly in steps to about above 70°–80° C. This temperature applied for about 1 to 3 seconds is high enough to kill the follicles and/or the vessels feeding the follicles but not high enough to vaporize the oil. During this short period minimal heat is transferred to the skin tissue except that tissue immediately surrounding the follicle.

I have performed hair removal experiments using the parameters shown in Table 2 with excellent results. There is no significant pain. The hair is removed and there is no apparent detrimental effect.

I have performed a quantitative mathematical analysis in order to estimate heat absorption and temperature distribution in the hair and skin tissue. This analysis is shown in Table 3.

TABLE 2

Heating of hair and carbon oil suspension in hair duct.

| | |
|---|---|
| Repetition Rate | 33 pulses per second |
| Time between pulses | about 0.03 seconds |
| Hair duct diameter | 0.1 mm |
| Energy per Pulse | 0.1 J |
| Energy per second | (0.1 J) (33) = 33 J/sec = 3 W |
| Beam spot | 1 cm$^2$ |
| Hair spacing | 130 hairs/cm$^2$ |
| Distance between hairs | 0.1 cm = 1 mm |
| Assume ¼ of energy goes into hair duct | |
| Energy per hair per pulse | (0.1 J/130)/4 = 0.00016 J |
| Volume of hair duct | |
| Length 1 mm | |
| Diameter 0.1 mm | |
| Vol. $= l\pi \left(\dfrac{D}{2}\right)^2 =$ | $(0.1\ cm)\pi \left(\dfrac{0.01}{2}\right)^2 = 0.0000078\ cm^3$ |
| Density of oil and hair = | 0.9 gm/cm$^3$ |
| Mass of oil & hair | 0.000007 gm |
| Specific heat of oil & hair assume | 4 J/gm °C. |
| Temperature rise per pulse, | $\dfrac{0.00016\ J}{(0.000007\ gm)\,4\ J/gm\ °C.} \approx 5°\ C.$ |
| $\Delta T = \dfrac{Q}{mc}$ | |

Thus, under these assumptions each pulse would heat the carbon oil suspension roughly about 5° C. (The reader is cautioned that the above analysis is not the be relied on as a quantitative description of the process of heating the carbon oil suspension in the hair duct. For example, for many people the assumption that ¼ of the energy of each pulse goes into the hair duct is probably too high.)

Each pulse will also heat the skin in general. I do not have a good estimate of the portions of the energy of the pulse reflected, absorbed in the hair ducts and absorbed in the skin in general. However, we have assumed for this qualitative analysis that about ½ of the energy the laser pulse reflects, ¼ is absorbed in the hair ducts and ¼ is absorbed in the skin in general. If we assume that the skin is heated fairly uniformly to a depth of 0.2 cm, a skin density of 1 gm/cm$^3$ and a specific heat for the skin, of 4 J/cm° C. the 0.025 J pulse will heat this typical skin section about 0.04 degrees C. Based on these assumptions, the 60 pulses over about 2 seconds will give a general heating of about 2° C. Therefore, heat deposited generally to the skin is practically negligible. (Again, the reader is cautioned regarding the qualitative nature of this analysis. In practice I believe much of the energy from the pulse $CO_2$ laser is absorbed in a very thin layer of the surface possibly as thin as 0.1 mm depending on the dryness of the skin. In some cases a very thin layer of the skin is actually vaporized in the process, but this is usually the layer which consists of essentially dead cells which naturally flake off the skin surface. Also, since the epidermis is such a poor heat conductor the underlying layers of skin are typically protected from damage except those portions very close to the carbon oil suspension.)

However, heat from the hot carbon oil suspension will be transferred by conduction to the tissue surrounding the hair duct. I used the following relationship (see note 10 of Zwig & Wibber, IEEE Journal of Quantum Electronics, Vol. QE-23, No. 10 October (1987), Mechanical and Thermal Parameters In Pulsed Laser Cutting of Tissue) to estimate the heat spread from the hot carbon oil suspension in the duct:

$$\delta = \sqrt{K\tau}$$

where $\delta$ represents the thickness of a heated zone during a time $\tau$, K being the heat of conduction. Assuming K=1.44× $10^{-3}$ cm$^2$/S and using 0.03 sec as the time interval between pulses, we estimate that the heat spreads out by about 0.007 cm from the hair duct between each pulse. This is about equal to the radius of the hair duct so we assume that about one half of the temperature rise from each pulse is transferred to the surrounding tissue during the 0.03 second following each pulse. This means that the net increase the temperature of the carbon-oil suspension from each pulse will be roughly 2.5° C.

Figure 4A:
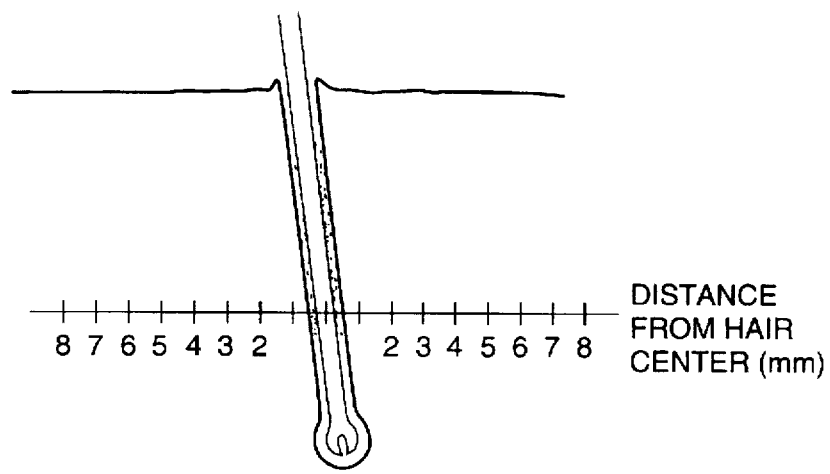
FIG. 4 A and B shows the temperature distribution near a typical hair during the process of a preferred embodiment of the present invention.
Figure 4B:
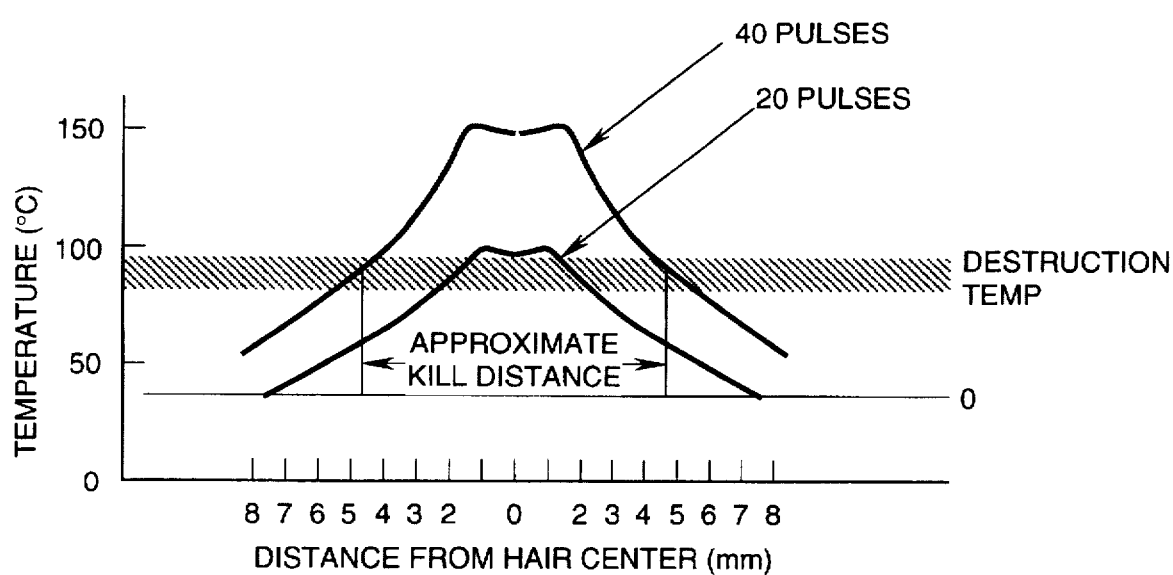

Thus, as depicted in FIG. 4 in about ⅔ second the temperature of the carbon-oil suspension in the hair duct has risen from a normal temperature of 37° C. to about 90° C., a temperature high enough to kill the follicle and the tissue cells immediately surrounding the hair follicle (i.e., within about ±5 hair diameter). In a little more than one second the temperature has risen to about 140° C. which I currently propose as the upper range. At this point the patient would begin to feel pain. Therefore, the illumination should be applied so that no spot is illuminated longer than about one second during one scan. FIGS. 4A and 4B shows a rough approximation of the temperature distribution between ±8 millimeters of the center for a typical hair duct after 20 and 40 pulses.

For my preferred process I illuminate a 10 cm$^2$ area by making 2 or 3 passes over each spot during a 20 second scanning period. For each spot the temperature will have dropped from the range of about 100° C. –140° C. to below about 50° C. during the approximately 7 seconds between scans.

As a result of the illumination, I estimate that essentially all follicles will be killed or will die within 2 weeks because of reduced nourishment due to the destruction of the tissue surrounding the hair duct which feed the follicle. I also estimate that the destruction tissue is confined to within about 1–2 millimeters (about 6–12 hair diameters) of the center of the hair.

SECOND PREFERRED EMBODIMENT

The 1.06 micron wavelength of the Nd:YAG laser penetrates the skin much better than the 10.6 micron CO$_2$ laser. By using the Nd:YAG laser we are able to concentrate more energy into the contaminant as compared to the skin in general. We can achieve hair removal with the Nd:YAG laser with parameters similar to those specified in the above describe embodiment by utilizing a non-Q-switched (of free running) mode.

THIRD PREFERRED EMBODIMENT

Very Short Pulses

An extremely important aspect of this invention is the reaction of carbon particles to exposure to very short high energy pulses of laser radiation. This reaction is depicted in FIGS. 5A through 5I. These figures depict a one micron particle held in place with transparent tape between two microscope slices and irradiated with a Nd:YAG laser beam.

Figure 5A:
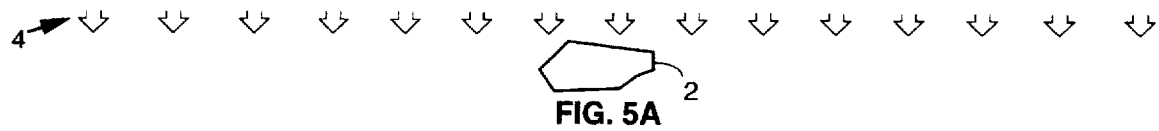
FIGS. 5A through 5I shows how graphite particles are fragmented under certain short pulse laser illumination.
Figure 5B:
Figure 5C:

In FIG. 5A a 1 micron particle is depicted being illuminated with a single laser pulse. The pulse is assumed to be produced with a Nd:YAG laser. The energy in each pulse is about 1.5 Joules. The cross sectional area of the pulse beam is 0.5 cm$^2$ so that the fluence (energy density) of the pulse is about 3 J/cm$^2$. The pulse is very short. The temporal width of the pulse at one-half maximum power is about 10 nanoseconds so that the peak power (pulse energy/pulse width) is about 150 megawatts. (By comparison the power output of a large nuclear power plant is about 1,000 megawatts but this is continuous.) The absorption coefficient of carbon for 1.06 micron Nd:YAG laser beam is very large. Essentially all of the beam is absorbed in a 0.1 micron layer of graphite. If we assume for a qualitative example a graphite cube 1 micron on each side, the energy illuminating the cube would be 3×10$^{-8}$ J. Therefore we estimate that the 1 micron particles absorbs about 3×10$^{-8}$ J. The volume of the cube is 1×10$^{-12}$ cm$^3$, the density of graphite is about 2 gm/cm$^3$ and the specific heat of graphite is 0.507 J/gm C. Therefore, the heat required to heat the particle from 25° C. to the sublimation temperature of graphite, about 3,652° C. is about 0.37×10–8 J. The heat of formation of carbon vapor from graphite at 25° C. is about 6×10$^4$ J/gm; therefore, the energy needed to vaporize all of the 1 micron particle is about 12×10$^{-8}$ J. Thus, the approximate 3×10$^{-8}$ J is absorbed many times that needed to heat the particle to its vaporization point, but the energy absorbed is only about 25 percent of the energy needed to vaporize it.

We have discovered that with these very short pulses of about 10 ns the particles are not merely heated but much of the energy of the pulse goes into fracturing violently the particles into two or more fragments. We suspect that the graphite crystal is heated to over 3000° C. and then easily fractured along its weak planes with these short high energy pulses. We do not know what portion of each particle vaporizes. Our tests prove the violent fracturing. Subsequent pulses continue to have the same impact on the smaller fragment particles. Thus, FIG. 1A shows a one micron particle 2 about to be illuminated with a 10 ns 3 J/cm$^2$ fluence of 1.06 micron laser pulse 4. In FIG. 1B a portion of the pulse is absorbed in particle 2 causing it to fracture violently as shown in FIG. 1C. The two particles have sufficient energy to travel several microns through the sticky substance of the transparent tape before coming to rest at a new location in the sticky substance of the tape.

Figure 5D:
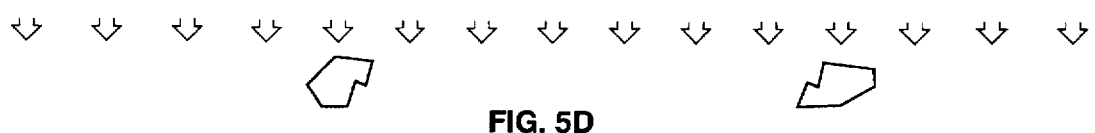
Figure 5E:
Figure 5F:
Figure 5G:
Figure 5H:
Figure 5I:

We assume that the beam is a 10 Hz beam so 0.1 second later another pulse like the first one is coming along as shown in FIG. 5D and as shown in FIG. 5E a portion of the pulse is absorbed in both halves of the original particle causing them to fracture violently as shown in FIG. 1F. The process repeats as shown in FIGS. 5G through 5I representing the 3rd pulse. For at least several of the subsequent pulses, qualitatively we estimate that all of the fragments of the original 1 micron particle will absorb on each pulse roughly about the same amount of energy as was absorbed by the original particle. After 5 pulses (assuming a 2 for 1 split in each case) our initial one micron particles would have split into 32 particles and the original particles and all of its daughter particles would have absorbed a total quantity of energy from the beam of about 5×3×10$^{-8}$ J or 15×10$^{-8}$ J. Most of this energy is very quickly dissipated in the form of heat increasing the temperature of the tissue surrounding the hair duct. This amount of energy 36×10$^{-8}$ J is enough to heat about 5×10$^{-10}$ grams of tissue to 100° C. This would correspond to about one tissue cell.

EXPERIMENT WITH SMALL PARTICLES

In order to confirm the above description I have conducted experiments in which these small carbon particles are irradiated with pulses of the type described above.

A small number of one micron size particles are placed in an enclosed glass vial in an air atmosphere and irradiated with pulses as described above. The particles are continuously broken into smaller and smaller particles and after about 10–15 pulses they vanish. I believe the very small particles are oxidized to form $CO_2$. When the same experiment is conducted in an argon atmosphere the particles continues to break into even smaller parts until they are border line invisible to the unaided eye (i.e. about 0.1 to 0.05 micron).

The above discoveries have lead to important improvements in my laser hair removal process.

The hair including the coated section was illuminated with 100 pulses of laser radiation from a Nd:YAG laser.

The following is a description of the pulsed laser beam:

| | |
|---|---|
| Wavelength | 1.06 micron |
| Energy per pulse | 1.5 Joules |
| Beam area | ½ cm² |
| Energy density | 3 J/cm² |
| Frequency | 10 pulses per second |

Each beam pulse 20 passed through the slides and chicken skin with no apparent effect. The beacon also passed through the wall of the vial and through the egg white.

The beam was scanned over the hair so that each portion of the hair received about 5 pulses. The beam had no effect on the hair or the egg white except near the section of the hair which was coated. In that section, the carbon in the mixture absorbed sufficient energy from the beam to cook the egg white immediately surrounding the coated section of the hair. In this experiment we could watch the cooking process because uncooked egg is transparent.

Figure 7A:
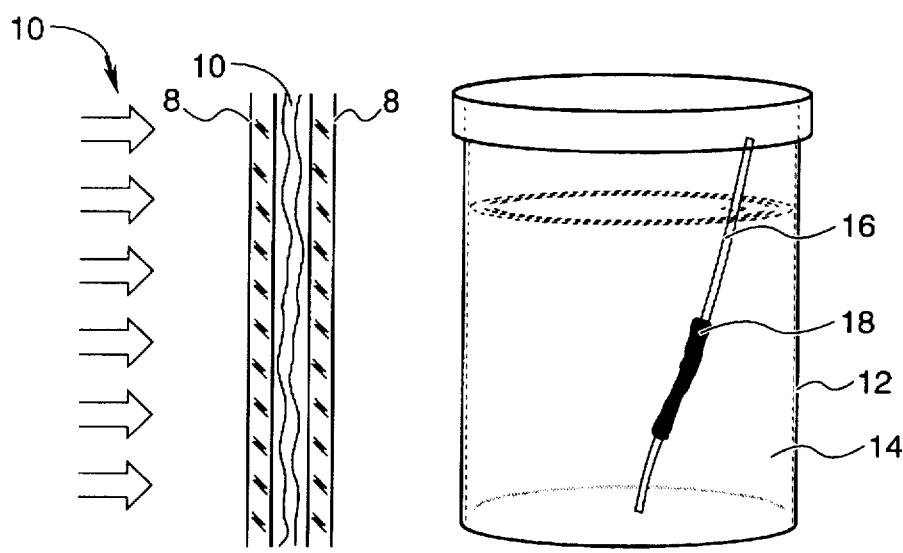
FIGS. 7A through 7C shows an experiment with turkey skin, egg white, a partially contaminated hair and a laser beam to demonstrate some of the elements of the present invention.
Figure 7B:
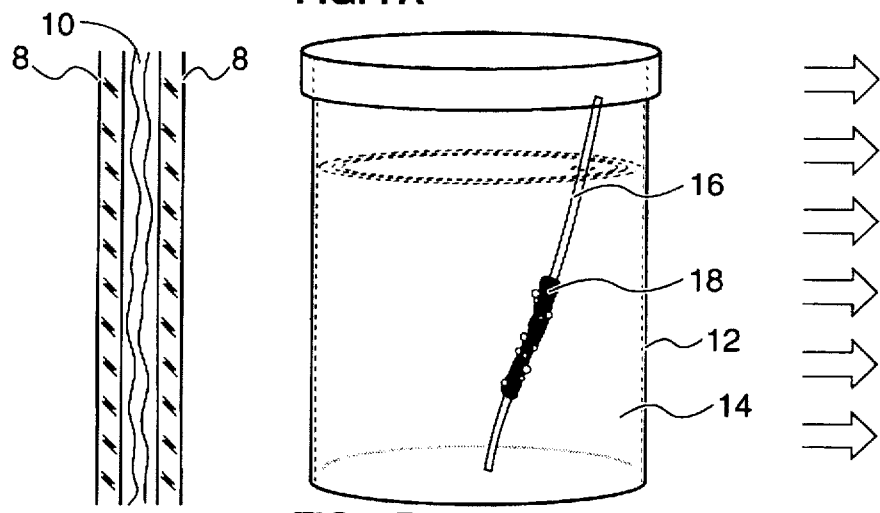
Figure 7C:
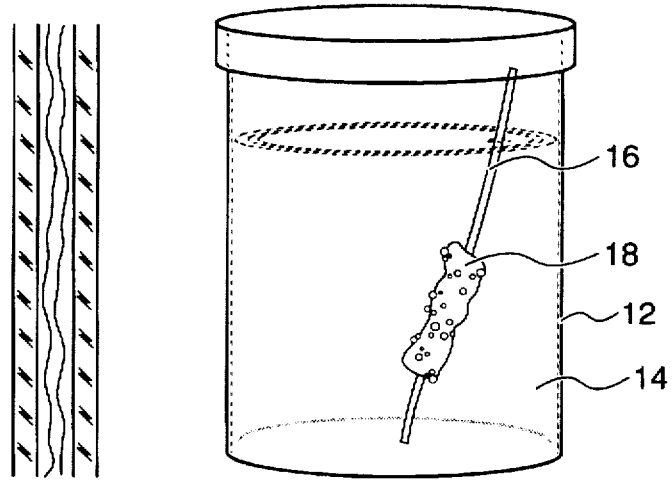

FIG. 7B shows the result of the first 10 pulses of beam 20 (about 3 pulses into the carbon) passing through the elements of this experiment. The only discernible effect of these pulses was an obvious heating and cooking of the egg white immediately adjacent to the coated section of the hair. Some fragments of the particle were thrown off the hair but were trapped in the immediate surrounding egg white. These fragments were further fragmented by subsequent pulses into very small fragments or oxidized. FIG. 7C shows the results of the 100 pulses. The egg white tissue in the immediate vicinity of the coated section was cooked to a thickness of about 500 micron. There was no damage discernible in either the turkey skin or anywhere else in the egg white or to the hair itself other than the coated section. These conclusions apparent to the unaided eye were checked and confirmed under a microscope. Only a very few small particles of carbon remained.

Hair Removal Process

My improved hair removal process has been successfully tested and demonstrated clinical trials at two medical clinics, one in California and one in New Jersey. The primary purpose of these

Footprint Defined

I have discovered that instead of cleaning the carbon-oil suspension off the surface of the skin prior to the laser illumination; a better result can be obtained by leaving a thin film of the carbon-oil suspension on the surface. The first one or two pulses will cause essentially all of the particles on the surface to break apart violently leaving a clean spot on the skin surface exactly defining the footprint of the laser beam. Therefore there is no doubt which area of the skin has been treated.

Scattering Particles Fill Duct (In air the effect of the beam illuminating a thin film of our carbon-oil mixture is that the particles are scattered widely, some to distances of more than one meter through he air.) A more important effect of the violent breaking apart of the small carbon particle is that many of the scattered fragments will penetrate deeply into the hair duct during the first 3 or 4 pulses as a result of the large amount of kinetic energy imparted to the fragments. Also the force of these tiny explosions imparts kinetic energy to unfractured particles. During subsequent pulses these fragments will be absorbing energy from the pulse at locations deep within the duct. The effect is shown graphically in FIGS. 6A through 6E and is discussed in the subsequent section entitled "Hair Removal Procedure." FIG. 6A represents 1 micron size particles before the first pulse. Note the size of particles shown in FIG. 6A compared to the hair which has a diameter of roughly 50 microns and extends under the surface of the skin for about 2 mm (or 2000 microns).

The space between the surface of the hair and the duct wall is a few microns (for example about 5 to 20 microns) wide and is normally filled with an oily film.

Hair in Egg White Experiment

FIGS. 7A, 7B and 7C describe an experiment I performed in order to demonstrate elements of my improved hair removal process. Three layers of turkey drumsticks skin 10 was sandwiched between two glass microscopic slides. The thickness of the 3 layers of turkey skin was about 2 millimeters (approximate depth of the bottom of human hairs). A single human hair 16 (one of my own) about 10 cm long was coated over a 3 cm section with a mixture 18 of 1 micron particles of carbon and mineral oil (about equal mass). The hair was immersed in chicken egg white 14 contained in a small (5 cm diameter) vial 12. The drawing is roughly to scale except the diameter of the hair and the carbon-oil contaminant is exaggerated.

trials was to test the safety and effectiveness of the process for removal of unwanted facial hairs, usually on the chin or upper lip area. The process used in these clinical trials is described below:

Carbon Mixture

In the process we use a mixture of one micron medical grade carbon (graphite) particles and mineral oil. The ratio is about 20 percent carbon and 80 percent mineral oil by weight.

Application of Mixture

The hair in the to-be-treated area is cut with a barber clipper to about a length of about 5 mm from the skin surface. The mixture is applied to the area to be treated. The mixture is massaged into the skin with a cotton swab until the hair ducts in the to-be-treated area are infiltrated to an estimated depth of about 20 microns. This stage of the process is depicted in FIG. 6A. In addition to the mixture infiltrated in the hair ducts, a thin film of the carbon-oil mixture (for example, about 100 particles per cm²) is left on the surface of the skin in the area to be treated.

Laser Illumination

The area to be treated is then illuminated with a pulsed laser beam from a Nd:YAG laser. The beam specifications are as follows:

| | |
|---|---|
| Wavelength | 1.06 micron |
| Energy per pulse | 1.5 Joules |
| Beam area | ½ cm² |
| Energy density | 3 J/cm² |
| Frequency | 10 pulses per second |

The beam is scanned over the area to be treated with each section of the skin in the area receiving about 5 pulses. The first or second pulses clean the mixture from the skin surface by violently fracturing the carbon particles so that the doctor is certain which area has been treated. As shown in FIG. 6A, the initial application of the carbon-oil mixture 25 results in carbon particles being deposited about 20 microns deep in the duct. FIG. 6B represents the results of the first pulse 30 shown in FIG. 6A. A shockwave in the mixture spreads out the mixture for several microns. More important, the violent fragmentation of the particles sends fragments through the duct. Additional pulses further fragment the particles and distribute the fragments further down the duct. (FIG. 6C shows qualitatively the distribution of particles after about 2 pulses.)

However, with each fragmentation, the particles get smaller (FIGS. 6D and 6E) and after about 4 or 5 pulses 30 through 36 the fragments have essentially disappeared. Essentially all of the energy absorbed by the particles and fragments is transferred to the skin tissue surrounding the hair. The net result is depicted in FIG. 6E. This energy is sufficient to devitalize the tissue feeding the hair so the hair dies. In FIG. 6A through 6E arrow 38 locates the section of skin tissue damaged. Our biopsy tests indicate the thickness of the damages sections range from zero to about 20 microns. The damage to the tissue appears to be the combined result of both the heating effect of the hot carbon particles and oil and some mechanical damage due to the kinetic energy of the particles and fragments.

Results

We have had excellent results with our human tests. In an early experiment with this improved process on my own leg essentially all hair was removed and after 26 months there has been no significant regrowth. Our clinical trials with facial hair have been on-going for about 26 weeks. We have been very conservative in the application of the laser beam, but the results are very good. No significant short term injury to the skin has been observed (only minor redness and in a very few cases some very minor bleeding). No long term injury has been observed. Hair removal success ratio in the treated area has ranged from about 0% to about 90% with the average being about 60%.

FOURTH PREFERRED EMBODIMENT

Removal of Hair from the Hair Ducts

Figure 8A:
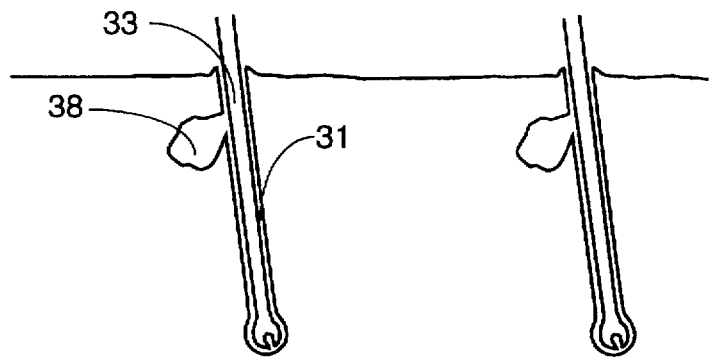
FIGS. 8A through 8C demonstrates a process using a depilatory to first remove part of the hair under the skin surface.
Figure 8B:
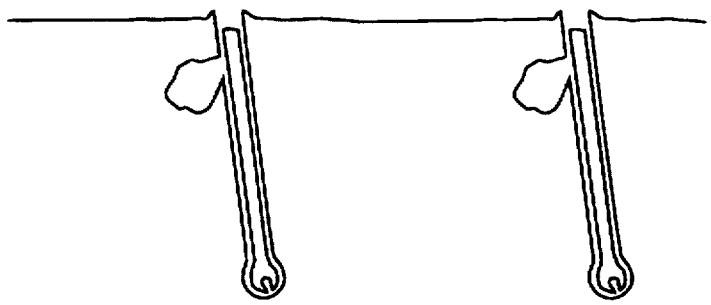
Figure 8C:
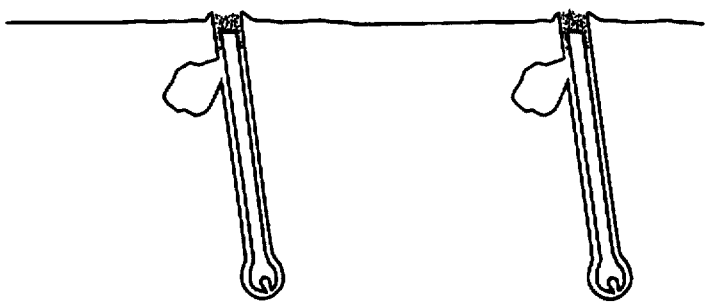

The amount of tissue destruction is highly dependent upon the amount of carbon contaminant in its hair duct. FIG. 8A depicts 2 hairs on a skin section showing hair stem 33, hair duct 31 and the sebaceous gland 38. As shown in FIG. 8B the hair is partially removed from the hair duct below the skin surface by chemical depilation. The carbon solution is then applied to the skin section and rubbed into the skin. In this case, since the upper part of the 50 micron diameter hair is gone, there is much more room in the duct for the solution with 1 micron particles as shown in FIG. 8C. The skin section is illuminated as discussed above but in this case the process is much more effective for hair tissue destruction and sebaceous gland tissue destruction because there is a far greater quantity of carbon particles initially in the duct.

Figure 9:
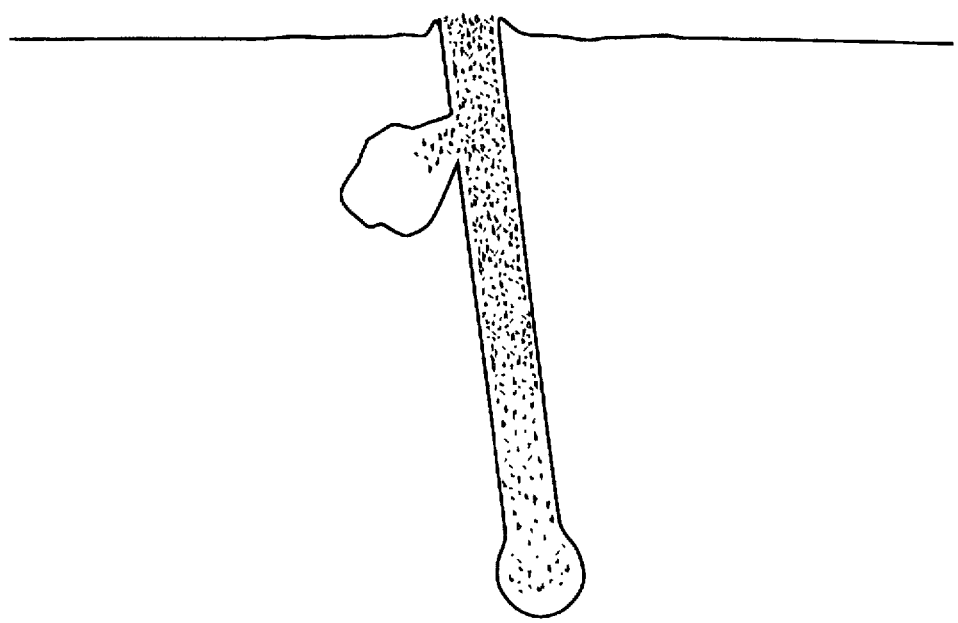
FIGS. 9 demonstrates complete removal of the hair prior to treatment.

FIG. 9 shows a hair duct in which the complete hair has been completely removed by a method such as plucking or by extraction with hair extraction wax. Here an even greater quantity of carbon particles can be infiltrated into the duct for even more effectiveness. A good method of removing the hair in preparation for the laser treatment is as follows:

Place a thin layer of super glue on a 2 cm² section of a glass microscope slide. After five seconds place the treated section of the slide on the skin area to be treated. Leave on the skin for 30 seconds. Lift the slide. This will pull out all hairs by the roots. The ducts can then be infiltrated with contaminant as discussed above.

FIFTH PREFERRED EMBODIMENT

Buckey Balls

Another potential method of increasing the quantity of contaminant in the hair duct is to use very small spherical particles. A carbon molecule meeting these specification has recently been produced and is available commercially. These molecules are known as buckey balls or $C_{60}$. Buckey balls are a carbon molecule, roughly spherical comprised of 60 atoms of carbon. Buckey balls are commercially available at prices of about $300 per gram. Our initial experiment with this form of carbon contaminant indicates very potentially promising results. The buckey balls are very absorptive of Nd:YAG laser beams and appear to infiltrate into the hair ducts very readily.

OTHER EMBODIMENTS

Persons skilled in the laser-medicine art will recognize that many other light source-contaminant combination could be used to practice this invention. The important attributes of the combinations are:

1) The light source must penetrate skin tissue.
2) The contaminant must be very highly absorptive of energy at the wavelength of the beam.
3) The contaminant should be capable of being infiltrated in significant quantities into the hair ducts.
4) Sufficient energy must be transferred to the contaminant to cause destruction of enough skin tissue to provide at least long term destruction of the hair.

Preferably the contaminant (like graphite) vaporizes at a very high temperature and during the illumination period absorbs enough laser energy to vaporize. These circumstances permit the contaminant to transfer heat to skin tissue while it is in its solid or liquid state and also while it is in its vapor state. Ultimate vaporization of the contaminant also serves the useful function of removing most of the contaminant from the duct during the treatment process. Fracturing contaminant into ever smaller particles is also a satisfactory process of effectively removing the particles. This is because small particles become invisible after a few fractures and once they are reduced to a small fraction of a micron the body's immune system can remove them.

Applicants have tested acrylic tattoo inks which have been approved by FDA for tattoo use. Black and blue tattoo inks marketed by Spaulding and Rogers appear to work well with a Nd:YAG laser operating at 1 Hz, 1.06 micron with an energy density of about 3 J/cm². We had less success with other colors.

While the above description contains many specifications, the reader should not construe these as limitations on the scope of the invention, by merely as exemplifications of preferred embodiments thereof. Those skilled in the art will envision many other possible variations are within its scope. Accordingly the reader is requested to determine the scope of the invention by the appended claims and their legal equivalents, and not by the examples which have been given.

I claim:

1. A process for inhibiting growth of a plurality of hairs growing in hair ducts on a section of human skin comprising the steps of:
   (a) applying to said hairs and skin section a contaminant having a high absorption at at least one frequency band of light, said application being performed in a manner so as to assure that at least a portion of said contaminant infiltrates into said hair ducts,
   (b) illuminating said skin section with a plurality of short pulses of light at said at least one frequency band, the first of said short pulses having sufficient energy to cause a plurality of explosions in said contaminant so as to spread said contaminant in said hair ducts and subsequent pulses having sufficient energy to cause further explosions in said contaminant to further spread said contaminant toward the base of said hair ducts, said explosions and energy transferred to and from said contaminant causing damage to skin tissue surrounding the base of said hair ducts so as to cause long term inhibition of growth of at least a portion of the hairs growing in said ducts.

2. A process as in claim 1 wherein said short pulses of light are provided by a Nd:YAG laser operating at a wave length of about 1.06 microns.

3. A process as in claim 1 wherein said contaminant comprises about 15% to about 20% concentration by volume of small particles.

4. A process as in claim 3 wherein a large portion of said small particles are small enough to penetrate said hair duct but larger than 1 micron.

5. A process as in claim 3 wherein a large portion of said small particles are small enough to penetrate said hair duct but larger than 0.5 micron.

6. A process as in claim 3 wherein said pulses are repeated until substantially all of the small particles have been exploded into fragments and substantially all of the fragments remaining in the hair ducts are smaller than about 0.1 micron.

7. A process as in claim 6 wherein said short pulses are continued until substantially all the fragments are smaller than 0.05 micron.

8. A process as in claim 3 wherein said particles are graphite particles.

9. A process as in claim 3 wherein said contaminant is applied in such a manner as to leave a thin film of contaminant on the surface of the skin section prior to illumination, and the first of said short pulses having sufficient energy to explode a substantial number of the particles in said thin film so as to define a footprint of said first pulse.

10. A process as in claim 3 wherein said short pulses define a pulse duration and the pulse duration measured at one half maximum power is no longer than about 50 nanoseconds.

11. A process as in claim 10 wherein said short pulses of light are provided by a Nd:YAG laser operating at a wave length of about 1.06 microns.

12. A process as in claim 11 wherein said laser is in free running mode.

13. A process as in claim 12 wherein said short pulses define a pulse duration and the pulse duration measured at one half maximum power is no longer than about 10 nanoseconds.

14. A process as in claim 12 wherein the beam of said laser has an energy density of about 3 J/cm$^2$ and the energy of each pulse is about 1.5 J.

15. A process as in claim 12 wherein the width of said pulses is from about 275 ns to about 200 µs.

16. A process as in claim 12 wherein the beam of said laser has a spot size of about 0.5 cm$^2$.

17. A process as in claim 12 wherein said pulses repeat at a frequency of about 10 Hz.

18. A process as in claim 1 wherein said short pulses of light are provided by a $CO_2$ laser operating at a wave length of about 10.6 microns.

19. A process as in claim 18 wherein said pulses repeat at a frequency of about 8 Hz to about 30 Hz.

20. A process as in claim 18 wherein the beam of said laser has a spot size of about 1 cm$^2$.

21. A process as in claim 18 wherein the beam of said laser is scanned over said skin section at a rate of about 20 to about 30 sec/10 cm$^2$.

22. A process as in claim 18 wherein the energy of each said pulses is about 1.5 J.

23. A process as in claim 1 wherein said contaminant comprises $C_{60}$.

24. A process as in claim 23 wherein a large portion of said small particles are small enough to penetrate said hair ducts but larger than 0.5 micron.

25. A process as in claim 23 wherein short pulses are repeated until substantially all of the small particles have been exploded into fragments and substantially all of fragments remaining in the hair ducts are smaller than 0.1 micron.

26. A process as in claim 25 wherein said short pulses are continued until substantially all the fragments are smaller than 0.05 microns.

27. A process as in claim 23 wherein said contaminant is applied in such a manner as to leave a thin film of contaminant on the surface of the skin section prior to illumination, and the first of said short pulses has sufficient energy to explode a substantial number of the particles in said thin film so as to define a footprint of said first pulse.

28. A process as in claim 23 wherein said short pulses define a pulse duration and the pulse duration measured at one half maximum power is no longer than about 30 nanoseconds.

29. A process as in claim 1 and further comprising the steps of removing a portion of said plurality of said hairs from within said hair ducts prior to applying said contaminant.

30. A process as in claim 1 and further comprising the step of extracting a plurality of said hairs prior to applying said contaminant.

31. A process for the inhibiting growth of a plurality of hairs growing in hair ducts on a section of human skin comprising the steps of:
   (a) applying to said hairs and skin section a contaminant comprising a very large number of small graphite particles, said application being performed in a manner so as to assure that at least a portion of said contaminant infiltrates into said hair ducts,
   (b) illuminating said skin section with a plurality of short pulses of light which is readily absorbed in graphite, the first of said short pulses having sufficient energy to cause a plurality of said graphite particles to explode into two or more fragments so as to spread said contaminant in said hair ducts and subsequent pulses having sufficient energy to cause a plurality of said fragments to further explode into additional fragments to further spread said contaminant towards the base of said hair ducts, said explosions and energy transferred to and from said particles and fragments causing damage to skin tissue surrounding the base of said hair ducts so as to inhibit growth of at least a portion of the hairs growing in said ducts.

32. A process for the destruction of a plurality of hairs growing in hair ducts on a section of human skin comprising the steps of:

(a) applying to said hairs and skin section a contaminant comprising small graphite particles, said application being performed in a manner so as to assure that at least a portion of said contaminant infiltrates into said hair ducts, (b) illuminating said skin section with a plurality of short pulses of light that is readily absorbed in graphite, the first of said short pulses having sufficient energy to cause a plurality of said graphite particles to explode into two or more fragments so as to spread said contaminant in said hair ducts and subsequent pulses having sufficient energy to cause a plurality of said fragments to further explode into additional fragments to further spread said contaminant towards the base of said hair ducts, said explosions and energy transferred to and from said particles and fragments causing damage to skin tissue surrounding the base of said hair ducts so as to destroy at least a portion of the hairs growing in said ducts.

33. A process as in claim 32 wherein said short pulses of light are provided by a Nd:YAG laser operating at a wave length of about 1.06 microns.

34. A process as in claim 33 wherein a large portion of said small particles are small enough to penetrate said hair ducts but larger than 0.5 micron.

35. A process as in claim 33 wherein said short pulses are repeated until substantially all of the small particles have been exploded into fragments and substantially all of the fragments remaining in the hair ducts are smaller than 0.1 micron.

36. A process as in claim 33 wherein said contaminant is applied in such a manner as to leave a thin film of contaminant on the surface of the skin section prior to illumination and the first of said short pulses has sufficient energy to explode a substantial number of the particles in said thin film so as to define a footprint of said first pulse.

37. A process as in claim 33 wherein said short pulses are continued until substantially all the fragments are smaller than 0.05 microns.

38. A process as in claim 33 wherein said short pulses define a pulse duration and the pulse duration measured at one half maximum power is no longer than about 10 nanoseconds.

39. A process as in claim 33 wherein said laser is in free running mode.

40. A process as in claim 39 wherein said short pulses define a pulse duration and the pulse duration measured at one half maximum power is no longer than about 10 nanoseconds.

41. A process as in claim 39 wherein the beam of said laser has an energy density of about 3 J/cm$^2$ and the energy of each pulse is about 1.5 J.

42. A process as in claim 39 wherein the width of said pulses is from about 275 ns to about 200 µs.

43. A process as in claim 39 wherein the beam of said laser has a spot size of about 0.5 cm$^2$.

44. A process as in claim 39 wherein said pulses repeat at a frequency of about 10 Hz.

* * * * *